(12) United States Patent
Oshima et al.

(10) Patent No.: US 12,146,649 B2
(45) Date of Patent: Nov. 19, 2024

(54) AIR SUPPLY AND LIGHTING SYSTEM

(71) Applicant: OBAYASHI CORPORATION, Tokyo (JP)

(72) Inventors: Shuhei Oshima, Tokyo (JP); Atsuya Yuasa, Tokyo (JP); Sadayoshi Nomizo, Tokyo (JP); Takashi Seki, Tokyo (JP)

(73) Assignee: OBAYASHI CORPORATION, Tokyo (JP)

( * ) Notice: Subject to any disclaimer, the term of this patent is extended or adjusted under 35 U.S.C. 154(b) by 0 days.

(21) Appl. No.: 18/368,813

(22) Filed: Sep. 15, 2023

(65) Prior Publication Data

US 2024/0093864 A1    Mar. 21, 2024

(30) Foreign Application Priority Data

Sep. 20, 2022  (JP) .................................. 2022-148743
Sep. 20, 2022  (JP) .................................. 2022-148744

(51) Int. Cl.
*F21V 33/00*    (2006.01)
*A61B 90/30*    (2016.01)
*F21W 131/205*    (2006.01)

(52) U.S. Cl.
CPC .......... *F21V 33/0068* (2013.01); *A61B 90/30* (2016.02); *F21V 33/0088* (2013.01); *F21W 2131/205* (2013.01)

(58) Field of Classification Search
CPC ............. F21V 33/0068; F21V 33/0088; F21V 33/0064; A61B 90/30; A61B 2090/309; F21W 2131/205; F21W 2131/20; F21W 2131/202
See application file for complete search history.

(56) References Cited

U.S. PATENT DOCUMENTS

| | | | |
|---|---|---|---|
| 2,962,582 A * | 11/1960 | Croft ....................... | F21S 8/033 454/295 |
| 3,967,107 A * | 6/1976 | Junginger ............... | A61B 90/30 362/33 |
| 10,828,124 B2 * | 11/2020 | Geerlings ........... | F21V 33/0068 |
| 2015/0369455 A1 * | 12/2015 | Nieminen ............. | F21V 21/104 362/428 |
| 2018/0172258 A1 * | 6/2018 | Schreiber .................. | A61L 9/00 |
| 2021/0236232 A1 * | 8/2021 | Jesurun .................. | A61B 90/00 |

FOREIGN PATENT DOCUMENTS

JP    2019-088731 A    6/2019

* cited by examiner

*Primary Examiner* — Bao Q Truong
(74) *Attorney, Agent, or Firm* — Maschoff Brennan

(57) ABSTRACT

A system for a room with a ceiling is provided. Air supply equipment forms a laminar flow of clean air around a target by supplying the clean air downward from an outlet provided in a first area of the ceiling located directly above the target. Operating light equipment illuminates a working area on the target in a shadowless manner by multiple light sources provided in a second area around the first area. Surface light emitting equipment controls a surface light emitting member provided in a third area around the second area.

8 Claims, 4 Drawing Sheets

AIR SUPPLY AND LIGHTING SYSTEM

BACKGROUND

1. Field

The present disclosure relates to an air supply and lighting system.

2. Description of Related Art

A typical operating room is provided with air supply equipment for supplying clean air to an area around an operating table and operating light equipment for illuminating an operating field in a shadowless manner. For example, Japanese Laid-Open Patent Publication No. 2019-88731 discloses air supply equipment that is provided in a ceiling and supplies clean air to an operating table from above to form a laminar flow in a specified region (clean region) around the operating table. Operating light equipment includes an articulated arm coupled to a ceiling and a lighting device supported by the ceiling with the articulated arm.

In the operating light equipment described in Japanese Laid-Open Patent Publication No. 2019-88731, it is necessary to adjust the articulated arm to dispose the lighting device near the operating field, that is, near the operator. For this reason, the articulated arm and the lighting device disturb the flow of clean air, which may make it impossible to ensure the cleanliness of the operating field. Similar to the case in which an operator performs an operation, the same problem also exists when a worker performs work on a work table or the like installed in a clean area, for example.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In a general aspect, a system for a room with a ceiling includes air supply equipment, operating light equipment, and surface light emitting equipment. The air supply equipment is configured to form a laminar flow of clean air around a target by supplying the clean air downward from an outlet provided in a first area of the ceiling located directly above the target. The operating light equipment is configured to illuminate a working area on the target in a shadowless manner by multiple light sources provided in a second area around the first area. The surface light emitting equipment is configured to control a surface light emitting member provided in a third area around the second area.

In another general aspect, a system for a room with a ceiling includes operating light equipment, a location information obtaining device, and a controller. The operating light equipment is configured to illuminate a working area on a target in a shadowless manner by multiple light sources provided in a first area of the ceiling, the first area being located above the target. The location information obtaining device is configured to obtain object location information representing a location of an object in an area around the target. The controller is configured to execute a process that changes an illumination direction of each light source in accordance with the object location information.

Other features and aspects will be apparent from the following detailed description, the drawings, and the claims.

BRIEF DESCRIPTION OF THE DRAWINGS

Throughout the drawings and the detailed description, the same reference numerals refer to the same elements. The drawings may not be to scale, and the relative size, proportions, and depiction of elements in the drawings may be exaggerated for clarity, illustration, and convenience.

DETAILED DESCRIPTION

This description provides a comprehensive understanding of the methods, apparatuses, and/or systems described. Modifications and equivalents of the methods, apparatuses, and/or systems described are apparent to one of ordinary skill in the art. Sequences of operations are exemplary, and may be changed as apparent to one of ordinary skill in the art, except for operations necessarily occurring in a certain order. Descriptions of functions and constructions that are well known to one of ordinary skill in the art may be omitted.

Exemplary embodiments may have different forms, and are not limited to the examples described. However, the examples described are thorough and complete, and convey the full scope of the disclosure to one of ordinary skill in the art.

An air supply and lighting system 10 according to an embodiment will now be described with reference to FIGS. 1 to 4.

Figure 1:
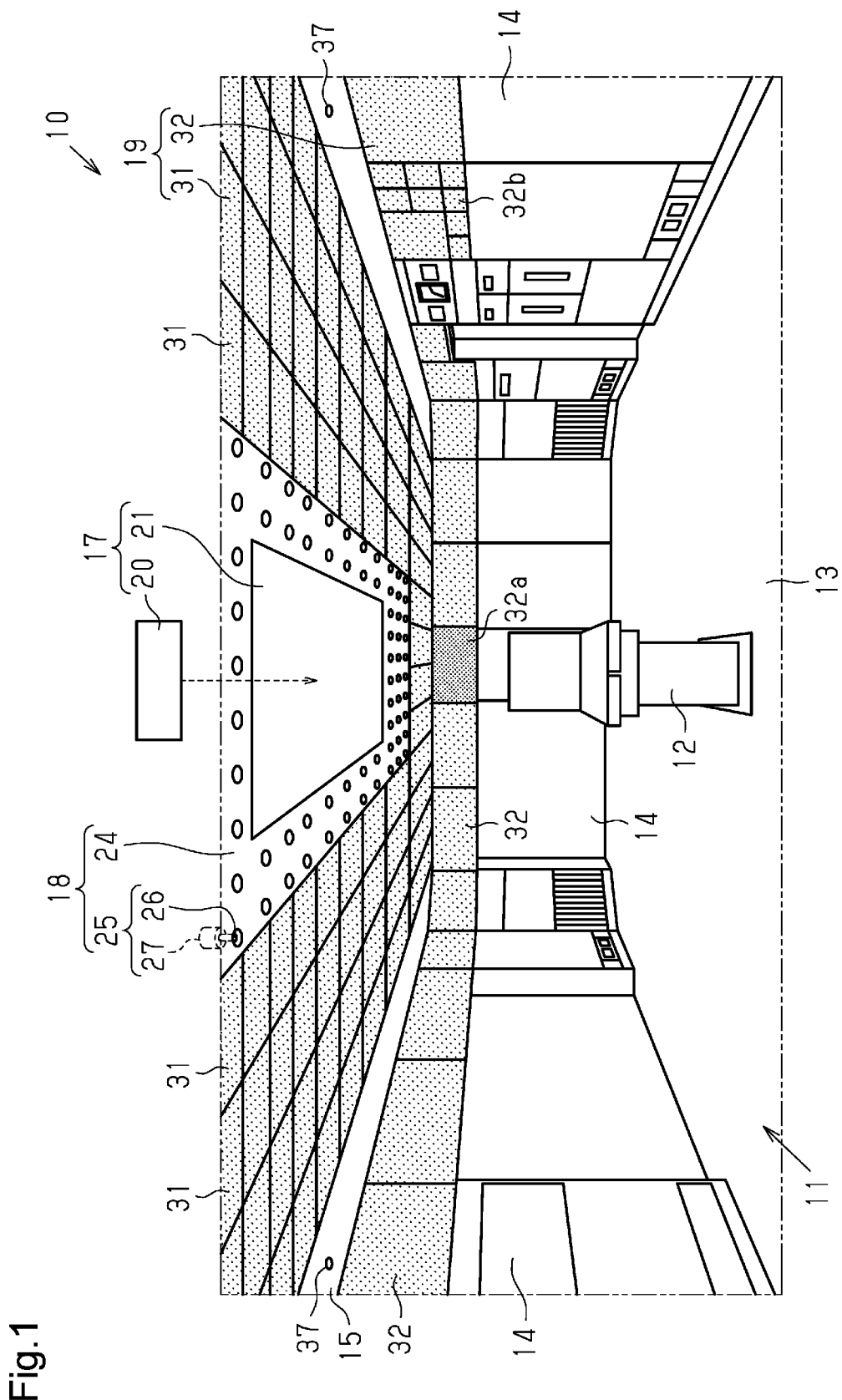
FIG. 1 is a diagram schematically showing an air supply and lighting system according to an embodiment.

As shown in FIG. 1, the air supply and lighting system 10 is installed in, for example, an operating room 11. The air supply and lighting system 10 is a system used in an operating room 11 to form, in a specified region (clean region), a laminar flow of clean air flowing down from above to an area around an operating table 12, which is a target of air supply and lighting. The air supply and lighting system 10 also illuminates an area including the operating table 12. The operating room 11 includes a floor 13, walls 14, and a ceiling 15. The walls 14 are connected to the floor 13 and the ceiling 15. The walls 14 are provided with an operation timer or the like for indicating the current time, the elapsed time, anesthesia time, and the like.

The air supply and lighting system 10 includes air supply equipment 17, operating light equipment 18, and surface light emitting equipment 19.

The air supply equipment 17 forms a laminar flow of clean air flowing from the ceiling 15 toward the floor 13 around the operating table 12. The air supply equipment 17 includes a clean air supplying device 20 and an outlet area 21.

The clean air supplying device 20 takes in and cleans air around the device 20, and then supplies the clean air to the outlet area 21.

The outlet area 21 is provided in the ceiling 15. Specifically, the outlet area 21 is provided in a section of the ceiling 15 located immediately above the operating table 12. The outlet area 21 is provided to overlap with the operating table 12 and a peripheral region of the operating table 12 in a top view of the operating room 11. The outlet area 21 includes multiple outlets (not shown). The clean air supplied from the clean air supplying device 20 is blown out downward from the respective outlets of the outlet area 21.

The operating light equipment 18 illuminates an area including the operating table 12 in a shadowless manner. The illuminated area includes an operating field, which is a working area on the operating table 12 and is an area in which an operator, who is a worker, performs a procedure. The region illuminated in a shadowless manner by the operating light equipment 18 is referred to as an illuminated area. The operating light equipment 18 includes multiple light devices 25 installed in an operating light area 24. The operating light area 24 is provided to surround the outlet area 21 in the ceiling 15. Each light device 25 is an embedded light device that is at least partly embedded in the ceiling 15. The light devices 25 are arranged in a grid pattern in the operating light area 24.

Each light device 25 includes a light source 26 and a direction adjuster 27.

The light source 26 is, for example, a light-emitting diode (LED) light with a lens. The light source 26 emits illumination light having directivity and a specified illuminance toward the area including the operating table 12.

The direction adjuster 27 is controlled by a controller 36, which will be discussed below, to adjust the illuminance and the illumination direction of the light source 26. The direction adjuster 27 includes, for example, servo motors and a mechanism that changes the illumination direction of the light source 26 in response to driving of the servo motors. The illuminated area of the operating light equipment 18 can be adjusted by changing the direction of illumination of each light source 26.

When a switch (not shown) is turned on, the surface light emitting equipment 19 illuminates the inside of the operating room 11 with the same illuminance as the diffuse sky illuminance. The surface light emitting equipment 19 includes first surface light emitting members 31 and second surface light emitting members 32 as light devices.

The first surface light emitting members 31 are installed in the ceiling 15. The first surface light emitting members 31 are, for example, surface LED panels. The first surface light emitting members 31 are installed in the entire ceiling 15 to surround the operating light area 24. The first surface light emitting members 31 illuminate the inside of the operating room 11 by causing the entire panels to emit white light.

The second surface light emitting members 32 are provided in the walls 14. In the embodiment shown in FIG. 1, the multiple second surface light emitting members 32 are installed in the upper portions of the walls 14 so as to surround the operating room 11. Each second surface light emitting member 32 is, for example, an organic electroluminescence (EL) panel. The manner in which the second surface light emitting members 32 emit light is controlled by the controller 36, which will be discussed below. Specifically, the second surface light emitting members 32 are capable of illuminating the inside of the operating room 11 by causing the entire panels to emit white light, displaying images based on video signals from the controller 36, which will be discussed below. That is, at least some of the second surface light emitting members 32 are capable of functioning as a display showing images.

Figure 2:
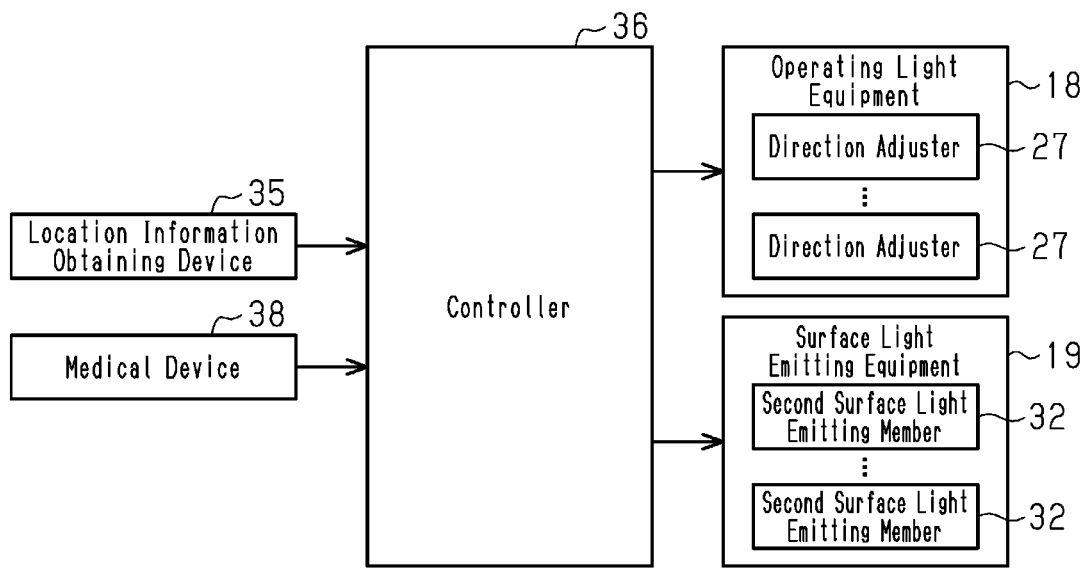
FIG. 2 is a block diagram showing an example of an electrical configuration of the air supply and lighting system.

As shown in FIG. 2, the air supply and lighting system 10 includes a location information obtaining device 35 and the controller 36.

The location information obtaining device 35 obtains location information of a target near the operating table 12 and outputs the obtained location information to the controller 36. The target is an operator, a medical device 38, or the like. The location information includes, in addition to information on the location illuminated by the light devices 25, information on the location and the shape of an object that is an obstacle to illumination by the light devices 25, and information on the location and the shape of an object between an operator and each second surface light emitting member 32. For example, as illustrated in FIG. 1, the location information obtaining device 35 includes multiple image capturing devices 37 installed in the ceiling 15. Each image capturing device 37 is installed above the operating table 12, and the imaging range of each image capturing device 37 includes the operating table 12. The location information obtaining device 35 obtains location information by performing an image recognition process on an image of the area including the operating table 12 captured by each image capturing device 37. The location information includes the location and the posture, the locations of the arms, and the hand positions of the operator, and the location and the shape of the medical device 38 near the operating table 12. An example of the medical device 38 is an angiography device that scans the operating table 12 to perform angiography of a patient.

A hardware configuration of the information processing device H10 functioning as the controller 36 will now be described with reference to FIG. 3.

Figure 3:
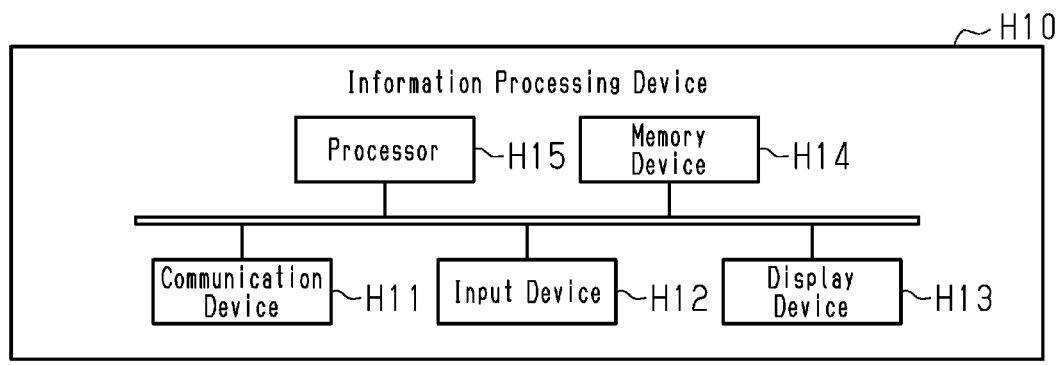
FIG. 3 is a block diagram showing an example of a hardware configuration of an information processing device functioning as the controller shown in FIG. 2.

As shown in FIG. 3, the information processing device H10 includes a communication device H11, an input device H12, a display device H13, a memory device H14, and a processor H15. This hardware configuration is merely one example, and the information processing device H10 may include other hardware.

The communication device H11 is an interface that establishes communication paths with other devices so as to transmit and receive data. The communication device H11 is, for example, a network interface or a wireless interface.

The input device H12 receives input from a user, and is, for example, a mouse, a keyboard, or a touch panel. The display device H13 is, for example, a display or a touch screen that displays various types of information.

The memory device H14 stores data and various programs used to perform various functions. Examples of the memory device H14 include a read-only memory (ROM), a random access memory (RAM), and a hard disk drive.

The processor H15 uses programs and data stored in the memory device H14 to control various processes. Examples of the processor H15 include, for example, a central processing unit (CPU) and a micro processor unit (MPU). The processor H15 loads programs stored in the ROM or the like into the RAM and executes various processes corresponding to various tasks.

The processor H15 is not limited to one that performs software processing on all processes executed by itself. For example, the processor H15 may include a dedicated hardware circuit (for example, an application specific integrated circuit: ASIC) that executes at least part of the processes executed by itself. That is, the processor H15 may be circuitry including: (1) one or more processors that operate according to a computer program (software), (2) one or more dedicated hardware circuits that execute at least part of various types of processes, or (3) a combination thereof. The processor includes a central processing unit (CPU) and memories such as a random-access memory (RAM) and a read-only memory (ROM). The memories store program codes or commands configured to cause the CPU to execute processes. Memory or computer-readable media includes any available media that can be accessed by a general purpose or special purpose computer.

As shown in FIG. 2, the controller 36 obtains location information from the location information obtaining device 35. The controller 36 executes a direction control process to control the illumination direction of each light device 25 based on the obtained location information.

In the direction control process, the controller 36, for example, identifies not only the location of the hand position of the operator based on the obtained location information, but also the medical device 38 located between the hand position and each light device 25. The controller 36 controls the direction adjuster 27 of each light device 25 such that the hand position, i.e. the operating field, is illuminated in a shadowless manner. When there are multiple operators, the controller 36 identifies not only the hand position of each operator but also the medical device 38 between each hand position and each light device 25. The controller 36 controls the direction adjuster 27 of each light device 25 such that the hand position of each operator is illuminated in a shadowless manner.

In the direction control, the controller 36 may change the illumination directions of all the light devices 25. Alternatively, the controller 36 may change the illumination direction of some light devices 25 selected in accordance with the hand position, and may keep the operating field illuminated by the remaining light devices 25.

In addition to biological information of a patient, image information such as an X-ray image and a captured image of an endoscope camera is input to the controller 36 from various medical devices 38. The controller 36 is configured to select, for each piece of information, one of the second surface light emitting members 32 to display that piece of information based on an instruction operation on input device H12.

The controller 36 may be configured to execute a selection process of automatically selecting one of the second surface light emitting members 32 (information display device) to display information based on the location information. Specifically, the controller 36 obtains the location and shape of the medical device 38 near the operating table 12 in addition to the location and the posture of the operator based on the location information, and displays the information on the second surface light emitting member 32 located at a location where the operator can easily see the information.

In addition, in the selection process, when the operation is being performed by multiple operators, the controller 36 obtains the location and the shape of the medical device 38 near the operating table 12 in addition to the location and the posture of each operator, and then identifies the positional relationship between each operator and the second surface light emitting members 32. For each operator, the controller 36 displays information on the second surface light emitting member 32 located at a location where the operator can easily see the information.

Through such an instruction operation and selection process, the controller 36 may display the biological information on a second surface light emitting member 32a and may display the image information on a second surface light emitting member 32b as shown in FIG. 1, for example. This allows various information to be displayed in locations that are easy for the operator to see.

Figure 4:
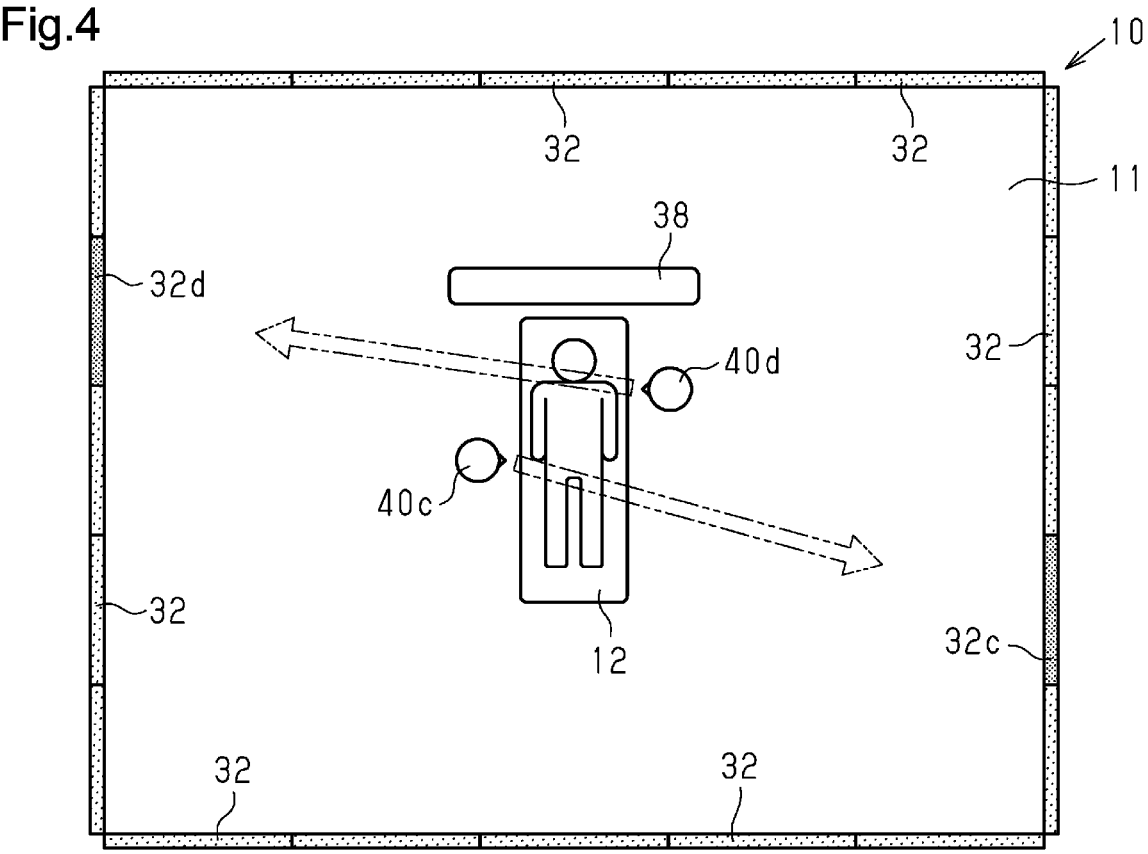
FIG. 4 is a diagram schematically showing an example of second surface light emitting members selected to be monitors by a selection process in a case in which there are multiple operators.

Specifically, as shown in FIG. 4, when the operation is being performed by multiple operators 40c, 40d, the controller 36 obtains the locations and the postures of the operators 40c, 40d as well as the location and shape of the medical device 38 near the operating table 12 based on the location information, and identifies the positional relationship between the operators 40c, 40d, the medical device 38, and the second surface light emitting members 32. Through the selection process, the controller 36 displays information on a second surface light emitting member 32c that is easy for the operator 40c to see and displays information on a second surface light emitting member 32d that is easy for the operator 40d to see.

In the above-described air supply and lighting system 10, the operating light equipment 18 is capable of illuminating the area including the operating table 12 in a shadowless manner, and the surface light emitting equipment 19 is capable of illuminating the entire operating room 11 with the same illuminance as the diffuse sky illuminance.

The present embodiment has the following advantages.

(1) In the air supply and lighting system 10, the operating light equipment 18 includes multiple light devices 25 installed around the outlet area 21. Accordingly, the multiple light devices 25 illuminate the operating table 12 obliquely from above, so that the area including the operating table 12 is in a shadowless manner. In addition, the surface light emitting equipment 19 includes the surface light emitting members 31, 32 installed on the ceiling 15 and the walls 14 to illuminate the inside of the operating room 11 with the same illuminance as the diffuse sky illuminance. This ensures sufficient illuminance in the operating room 11 including the operating field. Specifically, the air supply and lighting system 10 achieves illumination in a shadowless manner in the area including the operating table 12 and ensures sufficient illuminance in the operating room 11, without disposing articulated arms or lighting devices near the operating table 12. As a result, the flow of clean air is less likely to be disturbed around the operating table 12. Therefore, the cleanliness of the operating field is more reliably ensured.

(2) Various light devices, which are heat sources, are installed on the ceiling 15 and the walls 14. Therefore, the temperature around the operator is prevented from rising due to illumination. This achieves a uniform temperature distribution inside the operating room 11. Accordingly, difference in the sensible temperature between the operator and the staff other than the operator is reduced.

(3) When the operating light equipment is supported on the ceiling 15 with an articulated arm, the articulated arm is required to have an operation region in which the operating light equipment does not interfere with other medical devices 38. To ensure such an operation region, the ceiling 15 must be relatively high.

In this regard, since the air supply and lighting system 10 does not require an articulated arm, the required height of the ceiling 15 can be reduced. Since this reduces the space of the operating room 11, the capacity required for the air-conditioning equipment of the operating room 11 is reduced. This reduces the running cost of the operating room 11.

(4) Further, since the required height of the ceiling 15 is reduced, the story height required for the floor in which the operating room 11 is located is reduced. This increases the flexibility in installing the operating room 11 in a building, and reduces the construction costs of a building with the operating room 11.

(5) The surface light emitting equipment 19 includes the second surface light emitting members 32 installed on the walls 14. This readily ensures the illuminance in the operating room 11.

(6) Some of the second surface light emitting members 32 function as displays. This eliminates the need for an articulated arm for connecting a display for displaying biological information or the like to the ceiling 15. As a result, the cleanliness of the operating field is more reliably ensured.

(7) It is possible to change the area illuminated by the light devices 25 of the operating light equipment 18. Thus, an appropriate region can be illuminated in a shadowless manner.

(8) In the air supply and lighting system 10, the controller 36 changes the area illuminated by the light devices 25 based on the location information obtained by the location information obtaining device 35. This allows an appropriate region to be illuminated in a shadowless manner in accordance with movement of the operator and the location of the medical device 38.

(9) The controller 36 is configured to select one of the second surface light emitting members 32 to display various information. This allows various information to be displayed in locations that are easy for the operator to see.

The above-described embodiment may be modified as follows. The above-described embodiment and the following modifications can be combined as long as the combined modifications remain technically consistent with each other.

The location information obtaining device 35 may obtain location information using a transmitter. For example, the location information obtaining device 35 may obtain location information on an operator by a transmitter carried by the operator or a transmitter attached to the wrist of the operator. In addition, the location information obtaining device 35 may obtain location information on a medical device by a transmitter attached to the medical device. The transmitter attached to the medical device preferably transmits information including the shape of the medical device.

The operating light equipment 18 may be controlled so that the hands of the operator are included in the illuminated area. For example, the location information obtaining device 35 may output the coordinates of the hand position of the operator and the medical device in the operating room 11 to the controller 36 as location information, and the controller 36 may control the direction adjuster 27 of each light device 25 based on the coordinates. In this case, in addition to the coordinates of each location in the operating room 11, the controller 36 preferably stores manners in which the direction adjuster 27 is controlled in accordance with the coordinates. In addition, the air supply and lighting system 10 may control the operating light equipment 18 so that the hands of the operator are included in the illuminated area by using an infrared search and tracking system, which detects and recognizes the hand position of the operator by infrared rays and tracks the hand position.

The operating light equipment 18 can have any configuration if it can illuminate the area of the operating table 12 including the operating field in a shadowless manner. Therefore, the air supply and lighting system 10 does not necessarily need to include the location information obtaining device 35 and the controller 36 that stores a program related to tracking control.

When the light sources 26 of the operating light equipment 18 are LED lights with lenses, each of the light sources 26 may include multiple lenses. In this case, the illuminated area may be adjusted by the direction adjuster 27 of each light device 25, or the illuminated area may be adjusted by changing the direction of the lenses in each light source 26. When illumination light passes through the lenses, the illuminated area may be adjusted by changing the relative locations of the lenses with respect to each other. Furthermore, the illuminated area of the operating light equipment 18 may be changed manually or may be fixed.

The location of the second surface light emitting member 32 functioning as a display may be determined in advance.

The operation timer may be shown by the second surface light emitting member 32 functioning as a display.

Each second surface light emitting member 32 does not necessarily need to have a function as a display. In this case, surface LED panels can be used as the second surface light emitting members 32.

The surface light emitting equipment 19 may include only the first surface light emitting members 31 installed on the ceiling 15.

Figure 5:
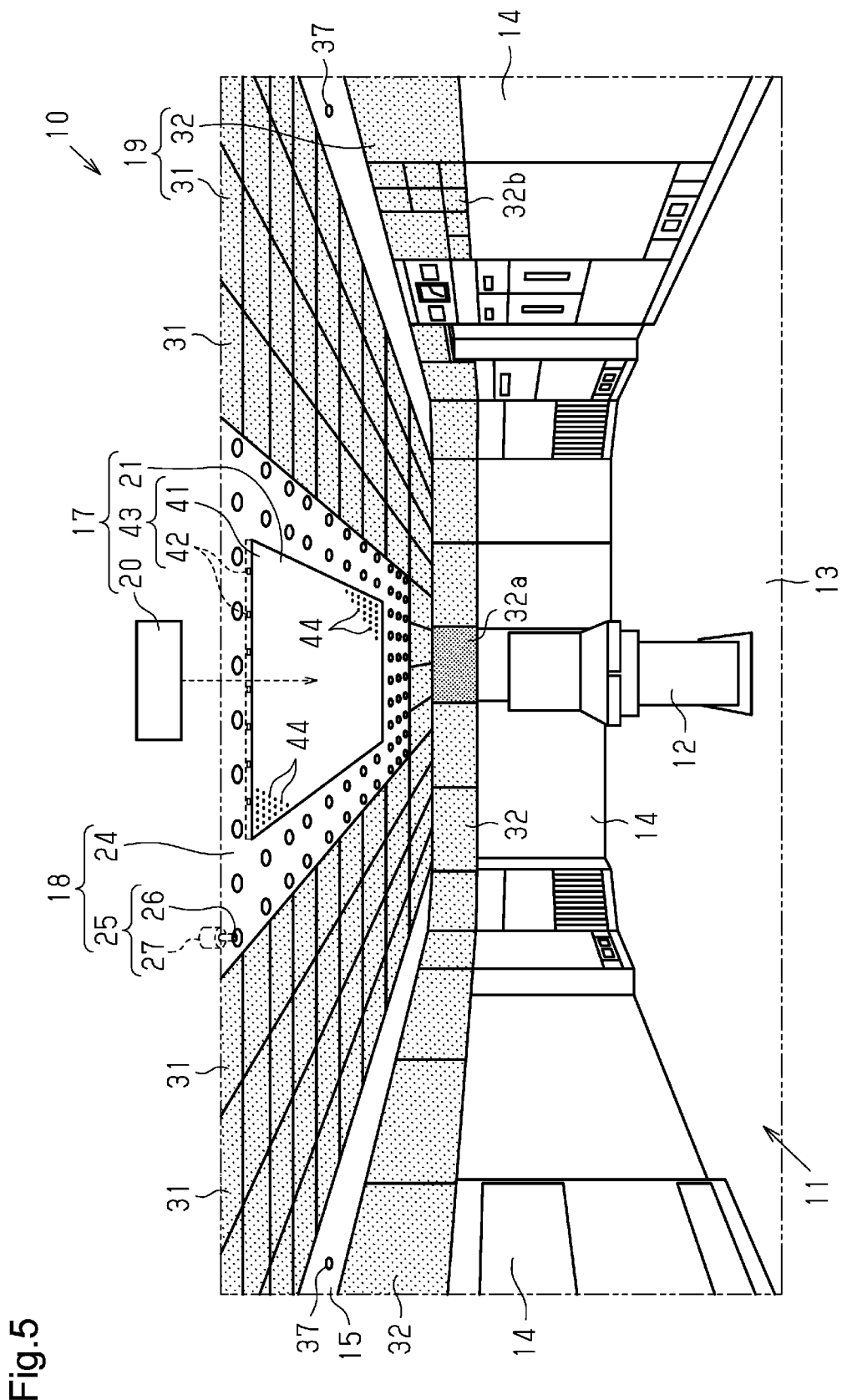
FIG. 5 is a diagram showing a schematic configuration of an air supply and lighting system according to a modification.

As shown in FIG. 5, the air supply equipment 17 may include an illuminator 43 including an optical waveguide 41 and waveguide light sources 42. The optical waveguide 41 includes outlets 44 and is installed in the outlet area 21. The optical waveguide light sources 42 are installed so that illumination light enters the optical waveguide 41 through side surfaces. The illumination light that enters the optical waveguide 41 is emitted from the inner peripheral surface of the outlets 44 to illuminate the area including the operating table 12. The direction, arrangement, and size of the air outlets 44 are designed so that clean air is uniformly supplied to the area around the operating table 12, and so that the illuminance of the area including the operating table 12 is uniform. FIG. 5 shows some the outlets 44 formed in the optical waveguide 41.

The air supply and lighting system 10 may have any configuration if the controller 36 can change the illumination direction of each light device 25 in accordance with the locations of the operator and the medical device 38 near the operating table 12. Therefore, the air supply equipment 17 is not essential to the air supply and lighting system 10. The operating light equipment 18 may also include a light device 25 located in a ceiling portion directly above the operating table 12.

In the air supply and lighting system 10 described above, the target of air supply and lighting is the operating table 12. The present disclosure is not limited to this. For example, the target of air supply and lighting may be a treatment table installed in an intensive care unit, an experiment table in a laboratory where various experiments are conducted, a work table in a workshop of a pharmaceutical factory where visual inspections of products are carried out, and a work table in an assembly room where electronic device assembly takes place.

Various changes in form and details may be made to the examples above without departing from the spirit and scope of the claims and their equivalents. The examples are for the sake of description only, and not for purposes of limitation. Descriptions of features in each example are to be considered as being applicable to similar features or aspects in other examples. Suitable results may be achieved if sequences are performed in a different order, and/or if components in a described system, architecture, device, or circuit are combined differently, and/or replaced or supplemented by other components or their equivalents. The scope of the disclosure is not defined by the detailed description, but by the claims and their equivalents. All variations within the scope of the claims and their equivalents are included in the disclosure.

The invention claimed is:

1. A system for a room with a ceiling, the system comprising:
air supply equipment configured to form a laminar flow of clean air around a target by supplying the clean air downward from an outlet provided in a first area of the ceiling located directly above the target;
operating light equipment configured to illuminate a working area on the target in a shadowless manner by multiple light sources provided in a second area around the first area; and
surface light emitting equipment configured to control a surface light emitting member provided in a third area around the second area, wherein
the surface light emitting member is a first surface light emitting member, and
the surface light emitting equipment is further configured to control a second surface light emitting member disposed on a wall connected to the ceiling.

2. The system according to claim 1, wherein
the second surface light emitting member is one of multiple second surface light emitting members, and
at least some of the second surface light emitting members are each configured to display an image.

3. The system according to claim 2, wherein
the target is an operating table, and
the working area is an operating field.

4. A system for a room with a ceiling, the system comprising:
operating light equipment configured to illuminate a working area on a target in a shadowless manner by multiple light sources provided in a first area of the ceiling, the first area being located above the target;
a location information obtaining device configured to obtain object location information representing a location of an object in an area around the target; and
a controller configured to execute a process that changes an illumination direction of each light source in accordance with the object location information, wherein
the location information obtaining device is configured to obtain worker location information representing a location of a worker, and
the controller is configured to change the illumination directions in accordance with the worker location information.

5. The system according to claim 4, wherein
the worker is one of multiple workers, and
the controller is configured to change the illumination directions in accordance with information indicating the location of each of the workers obtained by the location information obtaining device.

6. The system according to claim 4, wherein
the location information obtaining device is configured to obtain device location information representing a location of a device in an area around the target, and
the controller is configured to change the illumination directions in accordance with the worker location information and the device location information.

7. A system for a room with a ceiling, the system comprising:
operating light equipment configured to illuminate a working area on a target in a shadowless manner by multiple light sources provided in a first area of the ceiling, the first area being located above the target;
a location information obtaining device configured to obtain object location information representing a location of an object in an area around the target;
a controller configured to execute a process that changes an illumination direction of each light source in accordance with the object location information; and
surface light emitting equipment provided around the operating light equipment, the surface light emitting equipment including one or more surface light emitting members each configured to be switched between an illumination state, in which the surface light emitting member performs illumination, and a display state, in which the surface light emitting member displays an image, wherein
the location information obtaining device is configured to obtain worker location information representing a location of a worker, and
the controller is configured to select one of the one or more surface light emitting members in accordance with the worker location information and to switch the selected surface light emitting member to the display state.

8. The system according to claim 7, wherein
the target of illumination is an operating table, and
the working area is an operating field.

* * * * *